(12) United States Patent
Wilk

(10) Patent No.: US 6,582,444 B2
(45) Date of Patent: *Jun. 24, 2003

(54) BLOOD FLOW CONDUIT DELIVERY SYSTEM AND METHOD OF USE

(75) Inventor: Peter J. Wilk, New York, NY (US)

(73) Assignee: Percardia, Inc., Nashua, NH (US)

( * ) Notice: Subject to any disclaimer, the term of this patent is extended or adjusted under 35 U.S.C. 154(b) by 79 days.

This patent is subject to a terminal disclaimer.

(21) Appl. No.: 09/828,795

(22) Filed: Apr. 10, 2001

(65) Prior Publication Data

US 2002/0004662 A1 Jan. 10, 2002

Related U.S. Application Data

(63) Continuation of application No. 09/368,644, filed on Aug. 4, 1999, now Pat. No. 6,302,892.

(51) Int. Cl.$^7$ ................................. A61B 17/08
(52) U.S. Cl. ....................... 606/153; 128/898
(58) Field of Search ................. 606/108, 194, 606/195, 198, 153, 155; 623/1.1, 1.11; 128/898; 604/96.01, 164.01, 528, 8, 9, 10

(56) References Cited

U.S. PATENT DOCUMENTS

| | | | |
|---|---|---|---|
| 4,503,568 A | 3/1985 | Madras | |
| 4,665,918 A | 5/1987 | Garza et al. | |
| 5,122,154 A | 6/1992 | Rhodes | |
| 5,190,058 A | 3/1993 | Jones et al. | |
| 5,193,546 A | 3/1993 | Shaknovich | |

(List continued on next page.)

FOREIGN PATENT DOCUMENTS

| | | |
|---|---|---|
| EP | 0 903 123 | 3/1999 |
| EP | 0 938 870 | 9/1999 |
| EP | 0 956 825 | 11/1999 |

(List continued on next page.)

OTHER PUBLICATIONS

Gardner, M.D. et al., "An Experimental Anatomic Study of Indirect Myocardial Revascularization," *Journal of Surgical Research*, May 1971, vol. 11, No. 5, pp. 243–247.

(List continued on next page.)

*Primary Examiner*—Eduardo C. Robert
(74) *Attorney, Agent, or Firm*—Finnegan, Henderson, Farabow, Garrett & Dunner, LLP

(57) ABSTRACT

Described herein is a catheter system for delivering an L-shaped conduit into the body of a patient between the left ventricle and coronary artery. A shunt preferably made of semirigid material is inserted into the lumen of a delivery catheter. The delivery catheter is advanced within the patient until its distal end is located adjacent to the desired insertion site, which is preferably the junction between a coronary artery and passageway formed in the myocardium between the left ventricle and coronary artery. A proximal section of the shunt is first advanced out of the delivery catheter into the myocardial passageway. A distal section of the shunt is advanced into the coronary artery, preferably by advancing the distal section of the shunt into the myocardial passageway and then pulling the distal section back into the coronary artery, or by pushing the distal section of the shunt in a folded configuration out of the delivery catheter into the coronary artery. In one embodiment, the shunt is made of a collapsible material for insertion into the delivery catheter, the shunt expanding upon removal from the delivery catheter.

16 Claims, 7 Drawing Sheets

U.S. PATENT DOCUMENTS

| | | |
|---|---|---|
| 5,226,889 A | 7/1993 | Sheiban |
| 5,258,008 A | 11/1993 | Wilk |
| 5,287,861 A | 2/1994 | Wilk |
| 5,316,023 A | 5/1994 | Palmaz et al. |
| 5,330,486 A | 7/1994 | Wilk |
| 5,409,019 A | 4/1995 | Wilk |
| 5,429,144 A | 7/1995 | Wilk |
| 5,443,497 A | 8/1995 | Venbrux |
| 5,453,090 A | 9/1995 | Martinez et al. |
| 5,456,694 A | 10/1995 | Marin et al. |
| 5,456,712 A | 10/1995 | Maginot |
| 5,470,320 A | 11/1995 | Tiefenbrun et al. |
| 5,549,663 A | 8/1996 | Cottone, Jr. |
| 5,571,167 A | 11/1996 | Maginot |
| 5,607,444 A | 3/1997 | Lam |
| 5,632,762 A | 5/1997 | Myler |
| 5,643,278 A | 7/1997 | Wijay |
| 5,653,743 A | 8/1997 | Martin |
| 5,655,548 A | 8/1997 | Nelson et al. |
| 5,662,124 A | 9/1997 | Wilk |
| 5,676,670 A | 10/1997 | Kim |
| 5,709,713 A | 1/1998 | Evans |
| 5,733,267 A | 3/1998 | Del Toro |
| 5,755,682 A | 5/1998 | Knudson et al. |
| 5,758,663 A | 6/1998 | Wilk et al. |
| 5,797,920 A | 8/1998 | Kim |
| 5,797,933 A | 8/1998 | Snow et al. |
| 5,810,836 A | 9/1998 | Hussein et al. |
| 5,810,871 A | 9/1998 | Tuckey et al. |
| 5,824,071 A | 10/1998 | Nelson et al. |
| 5,825,040 A | 10/1998 | Cox |
| 5,830,222 A | 11/1998 | Makower |
| 5,878,751 A | 3/1999 | Hussein et al. |
| 5,904,697 A | 5/1999 | Gifford, III et al. |
| 5,908,028 A | 6/1999 | Wilk |
| 5,908,029 A | 6/1999 | Knudson et al. |
| 5,922,022 A | 7/1999 | Nash et al. |
| 5,944,019 A | 8/1999 | Knudson et al. |
| 5,951,599 A | 9/1999 | McCrory |
| 5,961,548 A | 10/1999 | Shmulewitz |
| 5,968,093 A | 10/1999 | Kranz |
| 5,971,993 A | 10/1999 | Hussein et al. |
| 5,976,153 A | 11/1999 | Fischell et al. |
| 5,976,155 A | 11/1999 | Foreman et al. |
| 5,976,178 A | 11/1999 | Goldsteen et al. |
| 5,979,455 A | 11/1999 | Maginot |
| 5,980,530 A | 11/1999 | Willard et al. |
| 5,980,533 A | 11/1999 | Holman |
| 5,980,552 A | 11/1999 | Pinchasik et al. |
| 5,980,553 A | 11/1999 | Gray et al. |
| 5,984,955 A | 11/1999 | Wisselink |
| 5,984,956 A | 11/1999 | Tweden et al. |
| 5,989,263 A | 11/1999 | Shmulewitz |
| 5,993,481 A | 11/1999 | Marcade et al. |
| 6,001,123 A | 12/1999 | Lau |
| 6,007,543 A | 12/1999 | Ellis et al. |
| 6,007,544 A | 12/1999 | Kim |
| 6,016,810 A | 1/2000 | Ravenscroft |
| 6,026,814 A | 2/2000 | LaFontaine et al. |
| 6,029,672 A | 2/2000 | Vanney et al. |
| 6,035,856 A | 3/2000 | LaFontaine et al. |
| 6,036,697 A | 3/2000 | DiCaprio |
| 6,039,721 A | 3/2000 | Johnson et al. |
| 6,042,581 A | 3/2000 | Ryan et al. |
| 6,053,924 A | 4/2000 | Hussein et al. |
| 6,053,942 A | 4/2000 | Eno et al. |
| 6,068,638 A | 5/2000 | Makower |
| 6,071,292 A | 6/2000 | Makower et al. |
| 6,076,529 A | 6/2000 | Vanney et al. |
| 6,080,163 A | 6/2000 | Hussein et al. |
| 6,081,738 A | 6/2000 | Hinohara et al. |
| 6,092,526 A | 7/2000 | LaFontaine et al. |
| 6,093,166 A | 7/2000 | Knudson et al. |
| 6,102,941 A | 8/2000 | Tweden et al. |
| 6,113,630 A | 9/2000 | Vanney et al. |
| 6,113,823 A | 9/2000 | Eno |
| 6,123,682 A | 9/2000 | Knudson et al. |
| 6,126,649 A | 10/2000 | VanTassel et al. |
| 6,139,541 A | 10/2000 | Vanney et al. |
| 6,159,225 A | 12/2000 | Makower |
| 6,182,668 B1 | 2/2001 | Tweden et al. |
| 6,186,972 B1 | 2/2001 | Nelson et al. |
| 6,187,034 B1 | 2/2001 | Frantzen |
| 6,190,353 B1 | 2/2001 | Makower et al. |
| 6,193,726 B1 | 2/2001 | Vanney |
| D438,618 S | 3/2001 | Solem |
| 6,196,230 B1 | 3/2001 | Hall et al. |
| 6,197,050 B1 | 3/2001 | Eno et al. |
| 6,213,126 B1 | 4/2001 | LaFontaine et al. |
| 6,214,041 B1 | 4/2001 | Tweden et al. |
| 6,223,752 B1 | 5/2001 | Vanney et al. |
| 6,231,587 B1 | 5/2001 | Makower |
| 6,237,607 B1 | 5/2001 | Vanney et al. |
| 6,248,112 B1 | 6/2001 | Gambale et al. |
| 6,250,305 B1 | 6/2001 | Tweden |
| 6,253,768 B1 | 7/2001 | Wilk |
| 6,253,769 B1 | 7/2001 | LaFontaine et al. |
| 6,254,564 B1 | 7/2001 | Wilk et al. |
| 6,258,119 B1 | 7/2001 | Hussein et al. |
| 6,261,304 B1 | 7/2001 | Hall et al. |
| 6,283,951 B1 | 9/2001 | Flaherty et al. |
| 6,283,983 B1 | 9/2001 | Makower et al. |
| 6,287,317 B1 | 9/2001 | Makower et al. |
| 6,290,728 B1 * | 9/2001 | Phelps et al. .................. 604/8 |
| 6,293,955 B1 | 9/2001 | Houser et al. |
| 6,302,875 B1 | 10/2001 | Makower et al. |
| 6,302,892 B1 | 10/2001 | Wilk |
| 6,306,125 B1 | 10/2001 | Parker et al. |
| 6,330,884 B1 | 12/2001 | Kim |
| 6,350,248 B1 | 2/2002 | Knudson et al. |
| 6,361,519 B1 | 3/2002 | Knudson et al. |
| 6,363,939 B1 | 4/2002 | Wilk |
| 6,375,615 B1 | 4/2002 | Flaherty et al. |
| 6,379,319 B1 | 4/2002 | Garibotto et al. |
| 6,387,119 B2 | 5/2002 | Wolf et al. |
| 6,390,098 B1 | 5/2002 | LaFontaine et al. |
| 6,395,208 B1 | 5/2002 | Herweck et al. |
| 6,406,488 B1 | 6/2002 | Tweden et al. |
| 6,406,491 B1 | 6/2002 | Vanney |
| 6,409,697 B2 | 6/2002 | Eno et al. |
| 6,409,751 B1 | 6/2002 | Hall et al. |
| 6,423,089 B1 | 7/2002 | Gingras et al. |
| 6,432,127 B1 | 8/2002 | Kim et al. |
| 6,447,522 B2 | 9/2002 | Gambale et al. |
| 6,447,539 B1 | 9/2002 | Nelson et al. |
| 6,458,323 B1 | 10/2002 | Boekstegers |
| 2001/0004699 A1 | 6/2001 | Gittings et al. |
| 2001/0012948 A1 | 8/2001 | Vanney |
| 2001/0016700 A1 | 8/2001 | Eno et al. |
| 2001/0025643 A1 | 10/2001 | Foley |
| 2001/0027287 A1 | 10/2001 | Shmulewitz et al. |
| 2001/0034547 A1 | 10/2001 | Hall et al. |
| 2001/0037149 A1 | 11/2001 | Wilk |
| 2001/0039426 A1 | 11/2001 | Makower et al. |
| 2001/0039445 A1 | 11/2001 | Hall et al. |
| 2001/0041902 A1 * | 11/2001 | Lepulu et al. ............... 606/153 |
| 2001/0047165 A1 | 11/2001 | Makower et al. |
| 2001/0053932 A1 | 12/2001 | Phelps et al. |
| 2002/0002349 A1 | 1/2002 | Flaherty et al. |
| 2002/0004662 A1 | 1/2002 | Wilk |
| 2002/0007138 A1 | 1/2002 | Wilk et al. |

| | | | |
|---|---|---|---|
| 2002/0029079 A1 | 3/2002 | Kim et al. | |
| 2002/0049486 A1 | 4/2002 | Knudson et al. | |
| 2002/0058897 A1 * | 5/2002 | Renati | 604/8 |
| 2002/0062146 A1 | 5/2002 | Makower et al. | |
| 2002/0065478 A1 | 5/2002 | Knudson et al. | |
| 2002/0072699 A1 | 6/2002 | Knudson et al. | |
| 2002/0077566 A1 | 6/2002 | Laroya et al. | |
| 2002/0092535 A1 | 7/2002 | Wilk | |
| 2002/0095111 A1 | 7/2002 | Tweden et al. | |
| 2002/0100484 A1 | 8/2002 | Hall et al. | |
| 2002/0111672 A1 | 8/2002 | Kim et al. | |
| 2002/0123698 A1 | 9/2002 | Garibotto et al. | |
| 2002/0165479 A1 | 11/2002 | Wilk | |

FOREIGN PATENT DOCUMENTS

| | | |
|---|---|---|
| EP | 1 097 676 A1 | 5/2001 |
| EP | 1 166 721 A2 | 1/2002 |
| GB | 2316322 | 10/1998 |
| WO | 94/16629 | 8/1994 |
| WO | 97/13463 | 4/1997 |
| WO | 97/13471 | 4/1997 |
| WO | 97/27893 | 8/1997 |
| WO | 97/27897 | 8/1997 |
| WO | 97/27898 | 8/1997 |
| WO | 97/32551 | 9/1997 |
| WO | 97/41916 | 11/1997 |
| WO | 97/43961 | 11/1997 |
| WO | WO 97/43961 | 11/1997 |
| WO | 98/06356 | 2/1998 |
| WO | 98/08456 | 3/1998 |
| WO | 98/10714 | 3/1998 |
| WO | 98/16161 | 4/1998 |
| WO | 98/19607 | 5/1998 |
| WO | WO 98/19607 | 5/1998 |
| WO | 98/44869 | 10/1998 |
| WO | 98/46115 | 10/1998 |
| WO | 98/46119 | 10/1998 |
| WO | 98/57591 | 12/1998 |
| WO | 99/08603 | 2/1999 |
| WO | 99/08624 | 2/1999 |
| WO | 99/17693 | 4/1999 |
| WO | 99/21490 | 5/1999 |
| WO | 99/22655 | 5/1999 |
| WO | 99/25273 | 5/1999 |
| WO | 99/32051 | 7/1999 |
| WO | 99/36000 | 7/1999 |
| WO | 99/36001 | 7/1999 |
| WO | 99/38459 | 8/1999 |
| WO | 99/40868 | 8/1999 |
| WO | WO 99/47078 | 9/1999 |
| WO | 99/47078 | 9/1999 |
| WO | 99/48427 | 9/1999 |
| WO | 99/48545 | 9/1999 |
| WO | 99/49790 | 10/1999 |
| WO | 99/49793 | 10/1999 |
| WO | 99/49910 | 10/1999 |
| WO | 99/51162 | 10/1999 |
| WO | 99/52481 | 10/1999 |
| WO | 99/53863 | 10/1999 |
| WO | 99/55406 | 11/1999 |
| WO | 99/60941 | 12/1999 |
| WO | 99/62430 | 12/1999 |
| WO | 00/09195 | 2/2000 |
| WO | 00/12029 | 3/2000 |
| WO | 00/15146 | 3/2000 |
| WO | 00/15147 | 3/2000 |
| WO | 00/15148 | 3/2000 |
| WO | 00/15149 | 3/2000 |
| WO | 00/15275 | 3/2000 |
| WO | 00/18302 | 4/2000 |
| WO | 00/21436 | 4/2000 |
| WO | 00/21461 | 4/2000 |
| WO | 00/21463 | 4/2000 |
| WO | 00/24449 | 5/2000 |
| WO | 00/33725 | 6/2000 |
| WO | 00/41632 | 7/2000 |
| WO | 00/41633 | 7/2000 |
| WO | 00/45711 | 8/2000 |
| WO | 00/56387 | 9/2000 |
| WO | 00/57814 | 10/2000 |
| WO | 00/66007 | 11/2000 |
| WO | 00/66009 | 11/2000 |
| WO | 00/66035 | 11/2000 |
| WO | 00/71195 | 11/2000 |
| WO | WO 01/10340 A1 | 2/2001 |
| WO | WO 01/10341 A2 | 2/2001 |
| WO | WO 01/10347 A1 | 2/2001 |
| WO | WO 01/10348 A1 | 2/2001 |
| WO | WO 01/10349 A1 | 2/2001 |
| WO | 01/17440 A1 | 3/2001 |
| WO | 01/49187 A1 | 7/2001 |

OTHER PUBLICATIONS

Palmaz et al., "Expandable Intrahepatic Portacaval Shunt Stents: Early Experience in the Dog," *AJR*, 1985, vol. 145, pp. 821–825.

Palmaz et al., "Expandable Intrahepatic Portacaval Shunt Stents in Dogs with Chronic Portal Hypertension," *AJR*, 1986, vol. 147, pp. 1251–1254.

Richter, M.D. et al., "Transjugular Intrahepatic Portacaval Stent Shunt: Preliminary Clinical Results," *Radiology*, 1990, vol. 174, No. 3, pp. 1027–1030.

Zemel, M.D. et al., "Percutaneous Transjugular Portosystemic Shunt," *JAMA*, 1991, vol. 266, No. 3, pp. 390–393.

Massimo, M.D. et al., "Myocardial Revascularization by a New Method of Carrying Blood Directly from the Left Ventricular Cavity into the Coronary Circulation," *Journal of Thoracic Surgeons*, Aug. 1997, vol. 34, No. 2, pp. 257–264.

Lary, M.D. et al., "Myocardial Revascularization Experiments Using the Epicardium," *Archives of Surgery*, Jan. 1969, vol. 98, No. 1, pp. 69–72.

Munro, M.D. et al., "The possibility of myocardial revascularization by creation of a left ventriculocoronary artery fistula," *Journal of Thoracic and Cardiovascular Surgery*, Jul. 1969, vol. 58, No. 1, pp. 25–32.

Kuzela, M.D. et al., "Experimental evaluation fo direct transventricular revascularization," *The Journal of Thoracic and Cardiovascular Surgery*, Jun. 1969, vol. 57, No. 6, pp. 770–773.

Burch et al., "Surgical closure of coronary artery fistula emptying into left ventricle," *American Heart Journal*, Jan. 1980, vol. 99, No. 1, p. 133.

Anabtawi, M.D. et al., "Experimental evaluation of myocardial tunnelization as a method of myocardial revascularization," *The Journal of Thoracic and Cardiovascular Surgery*, Nov. 1969, vol. 58, No. 5, pp. 638–646.

Vineberg et al., "Rapid Development in Dogs of Intramyocardial Vascular Pathways After Implantation of Bloodless Omental Strips in the Right and left Ventricular Myocardium," *The Canadian Journal of Surgery*, vol. 11, Apr. 1998, pp. 219–229.

Tala, M.D. et al., "Reappraisal of internal mammary arterio–venous fistula in experimental myocardial revascularization," *The Journal of Cardiovascular Surgery*, 1968, pp. 201–206.

Urschel, Jr. M.D. et al. "Direct and indirect myocardial revascularization: Follow–up and appraisal," *Surgery*, Dec. 1970, pp. 1087–1100.

Tweden et al., "Vetriculocoronary Artery Bypass (VCAB), a Novel Approach to Myocardial Revascularization," #2000–4653, Feb. 2000.

* cited by examiner

BLOOD FLOW CONDUIT DELIVERY SYSTEM AND METHOD OF USE

CROSS REFERENCE TO RELATED APPLICATIONS

This is a continuation of U.S. application Ser. No. 09/368,644, filed Aug. 4, 1999 now U.S. Pat. No. 6,302,892, which is incorporated herein by reference.

BACKGROUND OF THE INVENTION

1. Field of the Invention

The present invention relates to the delivery of a shunt and other devices into the myocardium of a patient, and more particularly, to the delivery of a generally L-shaped shunt to provide a bypass through the myocardium from the left ventricle into a coronary artery.

2. Description of the Related Art

Coronary arteries as well as other vessels frequently become clogged with plaque that at the very least impairs the efficiency of the heart's pumping action and can lead to heart attack and death. One conventional treatment for clogged coronary or other arteries is a bypass operation wherein one or more venous segments are inserted between the aorta and the coronary artery. The inserted venous segments or transplants act as a bypass of the clogged portion of the coronary artery and thus provide for a free or unobstructed flow of blood to the heart.

Such coronary artery bypass surgery, however, is expensive, time-consuming and traumatic to the patient. Hospital stays subsequent to the surgery and convalescence are prolonged.

A new coronary artery bypass technique is disclosed in U.S. Pat. No. 5,429,144. That technique utilizes a stent made of a biocompatible material and comprises steps of moving the stent in a collapsed configuration through a blood vessel of a patient's vascular system to the patient's heart, inserting the stent in the patient's myocardium, and upon disposition of the stent in the myocardium, expanding the stent from the collapsed configuration to a substantially tubular expanded configuration so that a blood flow path is formed at least partially through the myocardium.

U.S. Pat. No. 5,755,682 to Knudson discloses an L-shaped shunt (see FIG. 1A of Knudson) having one end in the lumen of an artery facing downstream from an obstruction and the other end in fluid communication with blood within the heart chamber. One problem with using this L-shaped shunt is how to get the shunt into the myocardium without undue trauma to the patient.

SUMMARY OF THE INVENTION

The problem of delivering an L-shaped shunt or conduit is solved herein by providing an improved catheter delivery system. A shunt preferably made of semirigid material is inserted into the lumen of a delivery catheter. The delivery catheter is advanced within the patient until its distal end is located adjacent to the desired insertion site, which is preferably the junction between a coronary artery and passageway formed in the myocardium between the left ventricle and coronary artery. A proximal section of the shunt is first advanced out of the delivery catheter into the myocardial passageway. A distal section of the shunt is advanced into the coronary artery, preferably by advancing the distal section of the shunt into the myocardial passageway and then pulling the distal section back into the coronary artery, or by pushing the distal section of the shunt in a folded configuration out of the delivery catheter into the coronary artery. In one embodiment, the shunt is made of a collapsible material for insertion into the delivery catheter, the shunt expanding upon removal from the delivery catheter.

In one aspect of the present invention, a method of delivering a conduit into a portion of the body having a first passageway and a second passageway joined generally at an angle is provided. A delivery catheter is advanced into the patient, the delivery catheter having a proximal end and a distal end and a lumen extending therethrough. The delivery catheter once advanced has a proximal end that extends outside of the patient and a distal end located substantially adjacent the location where the first passageway and the second passageway are joined. A conduit is inserted into the lumen of the delivery catheter, the conduit having a proximal section and a distal section. The proximal section of the conduit is advanced out of the lumen at the distal end of the delivery catheter into the first passageway. The distal section of the conduit is advanced into the second passageway.

In another aspect of the present invention, a method for creating a bypass between a chamber of the heart and a blood vessel adjacent to that chamber is provided. A passageway is formed in a heart wall that extends between the chamber of the heart and the blood vessel. The passageway has a proximal end opening into the chamber of the heart and a distal end opening into the blood vessel. A conduit is advanced having a proximal end and a distal end through the distal end of the passageway toward its proximal end. The proximal end of the conduit once advanced extends past the heart wall into the chamber of the heart, and the distal end of the conduit once advanced is located in the heart wall. The distal end of the conduit is advanced out of the distal end of the passageway and into the blood vessel downstream of the passageway.

In another aspect of the present invention, a method for creating a bypass between a chamber of the heart and a blood vessel adjacent to that chamber is provided. A passageway is formed in the heart wall that extends between the chamber of the heart and the blood vessel. The passageway has a proximal end opening into the chamber of the heart and a distal end opening into the blood vessel. A conduit having a proximal end and a distal end is folded to define a proximal section and a distal section between the fold. The folded conduit is inserted into a delivery catheter having a proximal end and a distal end and a lumen extending therethrough. The conduit is inserted such that the proximal end of the conduit is nearer to the distal end of the delivery catheter than the distal end of the conduit is to the distal end of the delivery catheter. Both the proximal end and the distal end of the conduit face toward the distal end of the delivery catheter. The delivery catheter is advanced into a patient into the blood vessel until its distal end is adjacent to the distal end of the passageway in the heart wall. The proximal section of the conduit is advanced out of the lumen at the distal end of the delivery catheter into the passageway. The distal section of the conduit is advanced out of the lumen at the distal end into the blood vessel.

DETAILED DESCRIPTION OF THE PREFERRED EMBODIMENTS

Figure 1A:
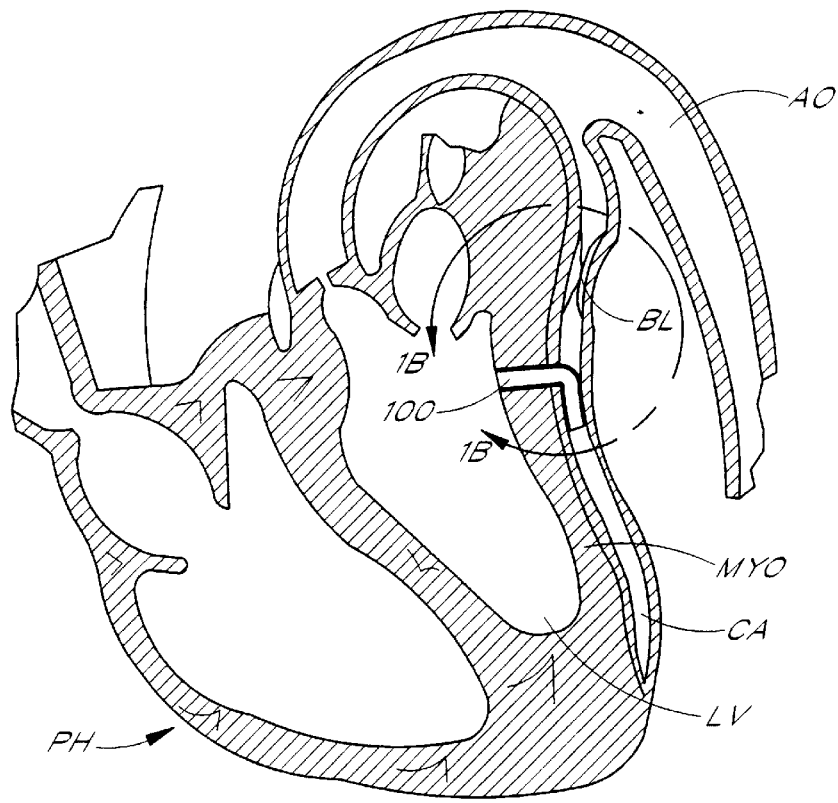
FIG. 1A is a schematic, cross-sectional view of a human heart, showing an L-shaped shunt device in the myocardium of the heart for forming a bypass between the left ventricle and a coronary artery.

The preferred embodiments described hereinbelow depict methods and apparatus for delivering a shunt into the myocardium to create a conduit between the left ventricle and coronary artery. Although the embodiments below describe delivery of an L-shaped shunt, it will be appreciated that these embodiments may also be applied to the delivery of similar types devices such as stents and other devices. Moreover, the methods and apparatus described herein may be used for delivery of these devices into other body tissues and vessels. For example, an L-shaped shunt may be delivered between other heart chambers to other coronary vessels. Although the term "L-shaped" is used herein for convenience, it will be understand that the shunt is merely generally L-shaped. Thus, the "L-shaped" shunt includes shunts that are angled, cornered, or simply change the direction of flow within the shunt from its proximal end to its distal end.

The principles of the present invention are not limited to left ventricular conduits, and include conduits for communicating bodily fluids from any space within a patient to another space within a patient, including any mammal. Furthermore, such fluid communication through the conduits is not limited to any particular direction of flow and can be antegrade or retrograde with respect to the normal flow of fluid. Moreover, the conduits may communicate between a bodily space and a vessel or from one vessel to another vessel (such as an artery to a vein or vice versa). Moreover, the conduits can reside in a single bodily space so as to communicate fluids from one portion of the space to another. For example, the conduits can be used to achieve a bypass within a single vessel, such as communicating blood from a proximal portion of an occluded coronary artery to a more distal portion of that same coronary artery.

In addition, the conduits and related methods can preferably traverse various intermediate destinations and are not limited to any particular flow sequence. Preferred embodiments are disclosed, including direct transmyocardial communication from a left ventricle, through the myocardium and into the coronary artery. The term "transmyocardial" should not be narrowly construed in connection with the preferred fluid communication conduits, and other non-myocardial and even non-cardiac fluid communication are preferred as well. With respect to the walls of the heart (and more specifically the term "heart wall"), the preferred conduits and related methods are capable of fluid communication through all such walls including, without limitation, the pericardium, epicardium, myocardium, endocardium, septum, etc.

The bypass which is achieved with certain preferred embodiments and related methods is not limited to a complete bypass of bodily fluid flow, but can also include a partial bypass which advantageously supplements the normal bodily blood flow. Moreover, the occlusions which are bypassed may be of a partial or complete nature, and therefore the terminology "bypass" or "occlusion" should not be construed to be limited to a complete bypass or a complete occlusion but can include partial bypass and partial occlusion as described.

The preferred conduits and related methods disclosed herein can also provide complete passages or partial passages through bodily tissues. In this regard, the conduits can comprise stents, shunts, or the like, and therefore provide a passageway or opening for bodily fluid such as blood. Moreover, the conduits are not necessarily stented or lined with a device but can comprise mere tunnels or openings formed in the tissues of the patient.

The conduits of the present invention preferably comprise both integral or one-piece conduits as well as plural sections joined together to form a continuous conduit. The preferred conduit device and method for installation is preferably determined by appropriate patient indications in accordance with sound medical practices.

Figure 1B:
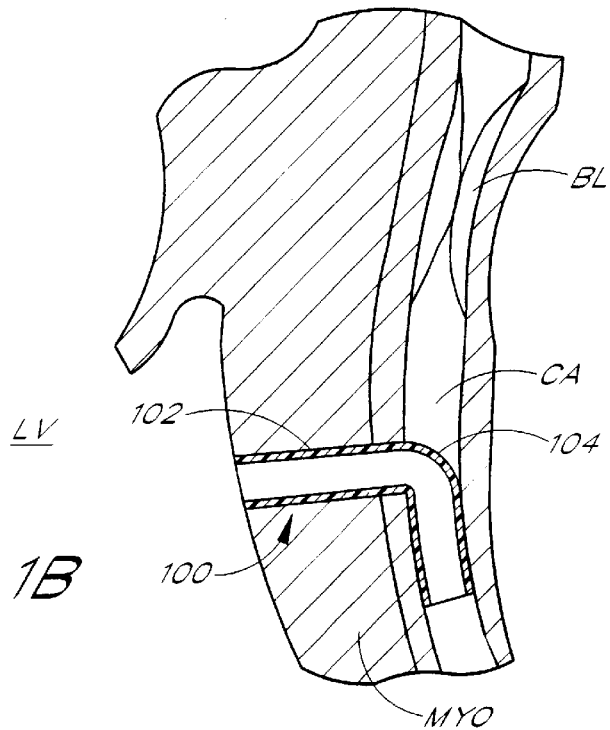
FIG. 1B is an enlarged view of the bypass shunt of FIG. 1A.
Figure 2:
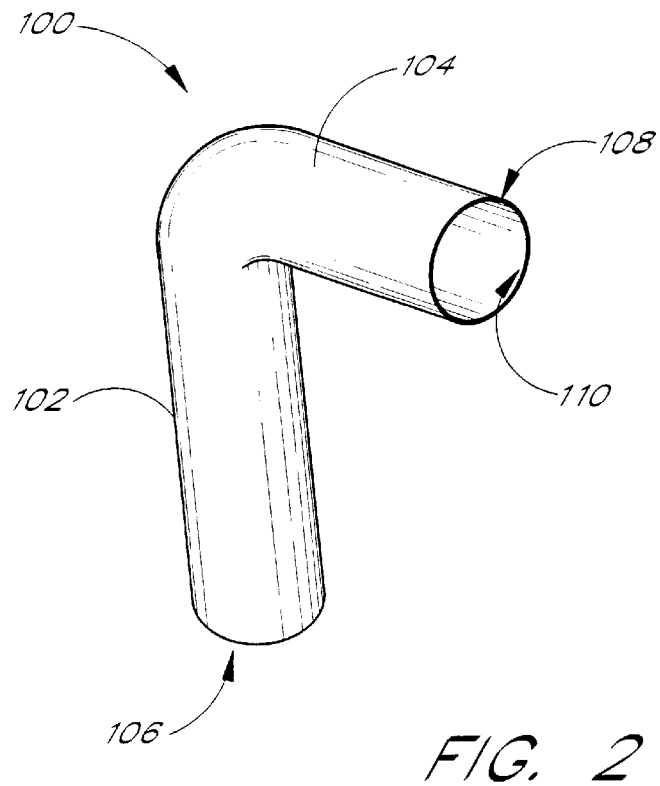
FIG. 2 is a perspective view of an L-shaped shunt according to one embodiment of the present invention.

As illustrated in FIGS. 1A and 1B, a coronary artery bypass is accomplished by disposing a conduit or shunt 100 in a heart wall or myocardium MYO of a patient's heart PH. As shown in FIG. 2, shunt 100 preferably has a first section 102 that extends from the left ventricle LV of heart PH to a clogged coronary artery CA at a point downstream of a blockage BL. Once inside the coronary artery CA, the shunt 100 bends to a second section 104 that extends downstream from the blockage BL. Although not shown in FIGS. 1A and 1B, shunt 100 may also have a one-way valve disposed therein for preventing back flow of blood through shunt, such as described in U.S. Pat. No. 5,429,144, the entirety of which is hereby incorporated by reference.

The shunt 100 illustrated in FIGS. 1A and 1B, and shown more particularly in FIG. 2, is preferably an elongate body having a proximal end 106 and a distal end 108 and a lumen 110 extending therethrough. Shunt 100 is preferably made of a semi-rigid biocompatible material such as biocompatible polymers, although other materials may also be used. The use of a semi-rigid material allows the shunt 100 to be easily folded into an L-shaped configuration, as shown in FIGS. 1A and 1B and described below. Further details regarding conduits or shunts such as described herein, as well as other medical devices and methods for use with the preferred embodiments of the present invention, are disclosed in copending applications entitled DESIGNS FOR LEFT VENTRICULAR CONDUIT, application Ser. No. 09/369, 048, filed Aug. 4, 1999, VALVE DESIGNS FOR LEFT VENTRICULAR CONDUITS, application Ser. No. 09/368, 393, filed Aug. 4, 1999, and LEFT VENTRICULAR CONDUITS TO CORONARY ARTERIES AND METHODS FOR CORONARY BYPASS, application Ser. No. 09/534, 038, filed Mar. 24, 2000, as well as U.S. Pat. Nos. 6,254,564, 5,662,124, 5,429,144 and 5,755,682, all of which are hereby incorporated by reference in their entirety.

Passageway Formation

In one preferred embodiment of the present invention, before delivery of the shunt 100, a passageway is formed at a desired location within the patient for placement of the shunt 100 within the patient. Although the formation of this passageway is described in a percutaneous approach, it will also be appreciated that surgical and other methods may be used as well.

Figure 3:
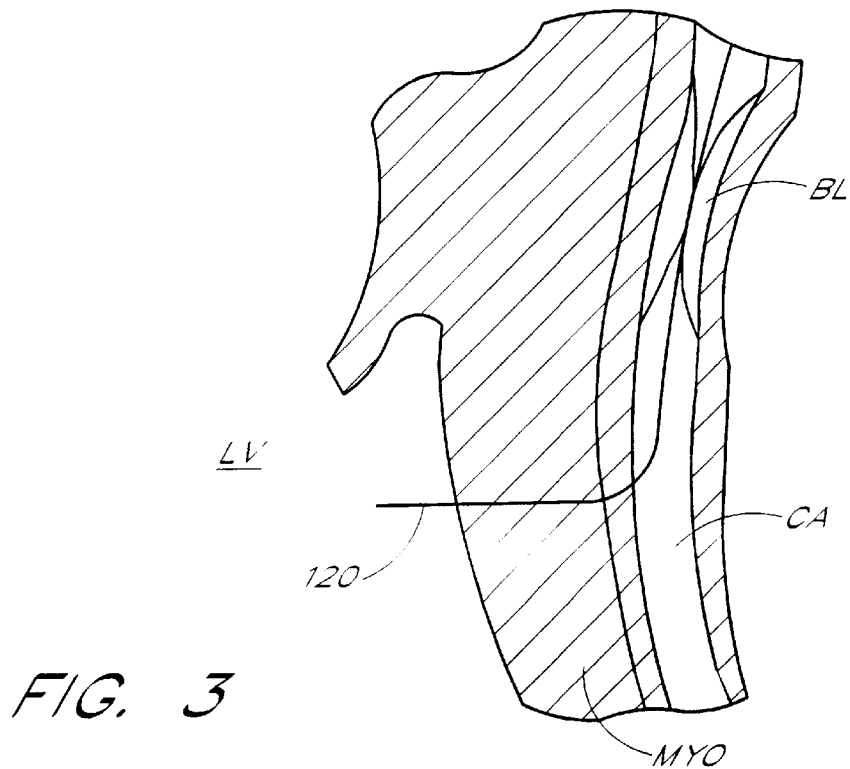
FIG. 3 is a schematic partial cross-sectional view of a coronary artery adjacent the left ventricle, showing a guidewire being advanced through an obstruction in the coronary artery.
Figure 4:
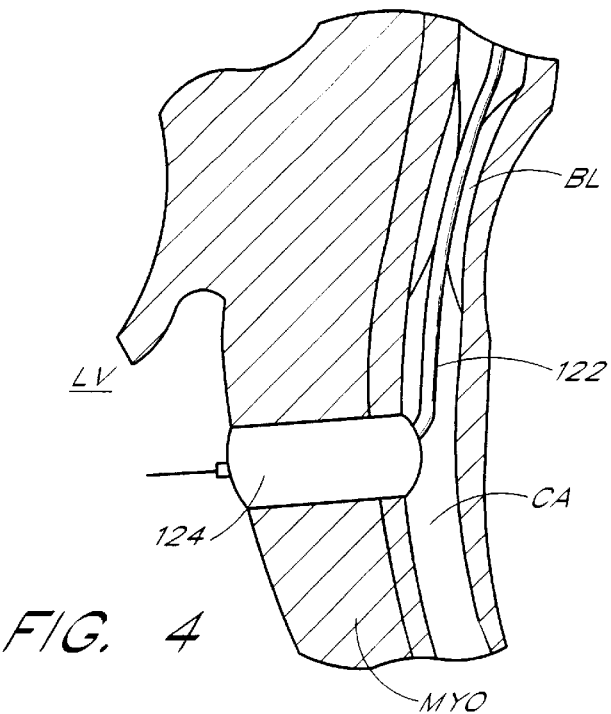
FIG. 4 is a schematic partial cross-sectional view of a coronary artery adjacent the left ventricle, showing a dilation catheter being advanced over the guidewire of FIG. 3 to create a myocardial passageway.
Figure 5:
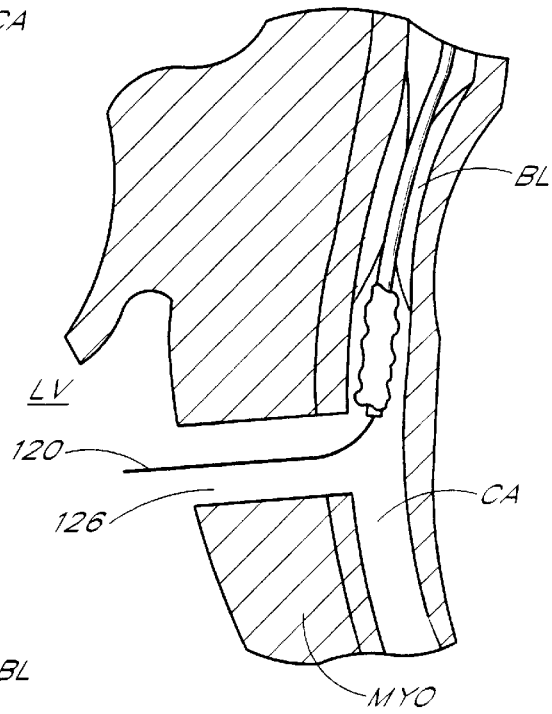
FIG. 5 is a schematic partial cross-sectional view of a coronary artery adjacent the left ventricle, showing the dilation catheter of FIG. 4 being retracted from the myocardium leaving a passageway through the myocardium.

FIGS. 3–5 illustrate the formation of a passageway 126 within the myocardium MYO of a patient extending between the left ventricle LV and the coronary artery CA. As shown in FIG. 3, a guidewire 120 is inserted into the coronary artery CA through the myocardium and into the left ventricle. This guidewire is preferably inserted into the patient through the femoral artery (not shown) and advanced percutaneously through aorta AO (shown in FIG. 1A) and through the blockage BL in the coronary artery, as is well known by those in the art. The guidewire then turns into the myocardium and extends therethrough, where it may be anchored at the left ventricle to the myocardium. Further details regarding these and other delivery methods are described in U.S. Pat. No. 6,261,304, issued Jul. 17, 2001, which is hereby incorporated by reference in its entirety.

After delivery of the guidewire 120, a dilation device 122, as shown in FIG. 4, is delivered over the guidewire 120 to open a passageway through the myocardium MYO. This dilation device 122 may employ radiation, lasers, balloons, successively larger catheters, a surgical drill or other methods to penetrate through the myocardium. FIG. 4 illustrates the use of a catheter 122 having a dilation balloon 124 mounted on the catheter for forming the passageway. The dilation catheter 122 is advanced over the guidewire 120, and the balloon 124 is inflated within myocardium MYO to expand the myocardial passageway 126, shown in FIG. 5. The balloon 124 is then deflated and the catheter 122 removed, as shown in FIG. 5, to leave the passageway 126 extending through the myocardium MYO. The process may be repeated with successively larger dilation balloons to form a passageway of desired size. Further details are described in the above-referenced U.S. Pat. No. 6,261,304, issued Jul. 17, 2001, the entirety of which is hereby incorporated by reference. It will be appreciated that other methods may also be used to form the passageway 126.

After formation of the passageway 126, the guidewire 120 may be removed for subsequent delivery of the shunt 100, or may remain in place to assist in the delivery as described below. It will be appreciated that other treatments known to one skilled in the art, such as angioplasty, may be used to reduce the size of the blockage BL before delivering the shunt.

Pullback Technique

In one embodiment of the present invention, the L-shaped shunt is delivered using a pullback technique. The term "pullback" is used for convenience only, and is not limited to pulling back only, but includes pushing and pulling of the shunt. According to this embodiment, a delivery catheter 100 is used to deliver the shunt 100 into a myocardial passageway such as formed in FIG. 5, or by any other method.

Figure 6:
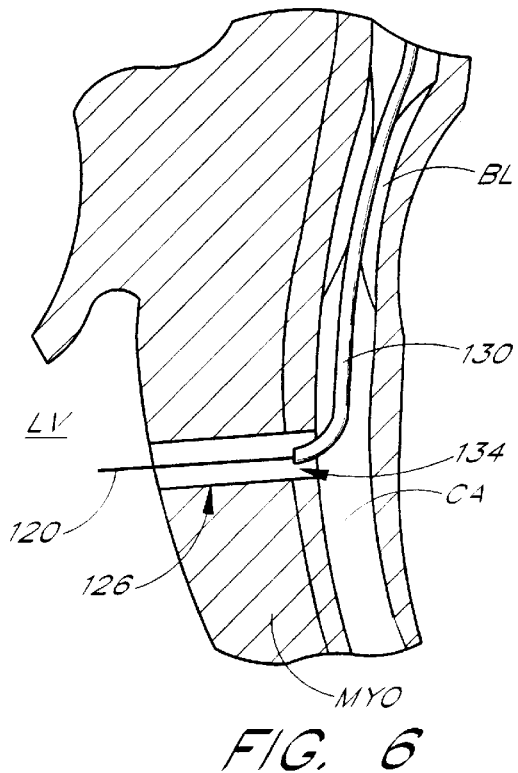
FIG. 6 is a schematic partial cross-sectional view of a coronary artery adjacent the left ventricle, showing a delivery catheter having a distal end positioned at least partially in the myocardial passageway of FIG. 5.

As shown in FIG. 6, a delivery catheter 130 is advanced over a guidewire 120, such as described above, toward the myocardium MYO. The delivery catheter 130 preferably has a proximal end 132 (not shown) extending outside of the patient and a distal end 134 extending at least partially within the passageway 126 formed in the myocardium MYO. More preferably, the distal end 134 of the delivery catheter 130, once delivered as shown in FIG. 6, turns into the passageway 126 so that the lumen 136 (not shown) of the delivery catheter faces into the passageway 126. After the delivery catheter has been placed in this position, the guidewire 120 may be removed to prevent interference with subsequent delivery of the shunt.

Figure 7:
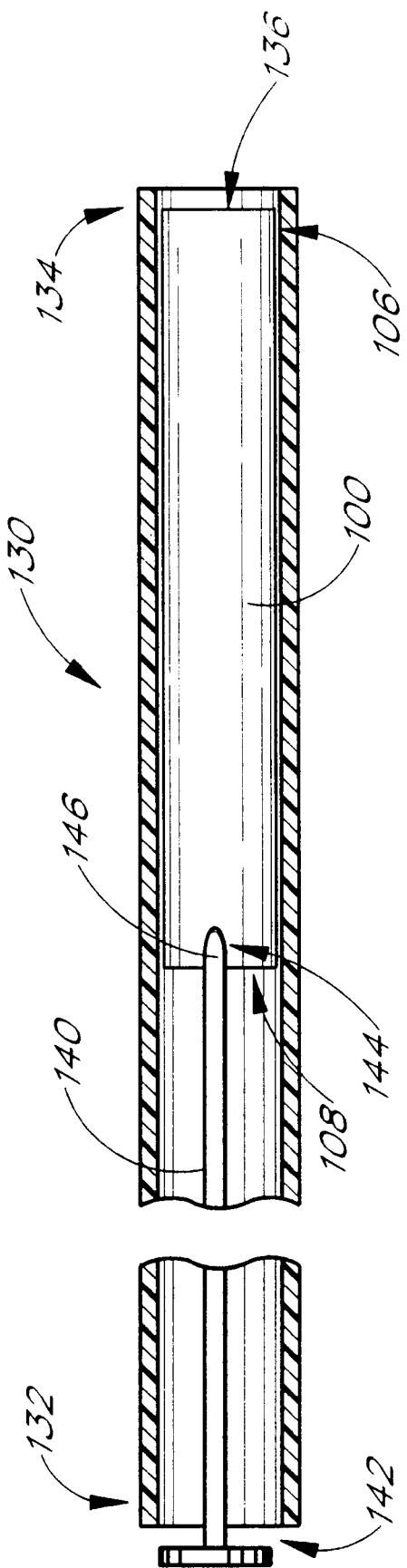
FIG. 7 is a partial cross-sectional view of the delivery catheter of FIG. 6 having a shunt inserted therein.

The shunt 100 is prepared for delivery into the passageway 126 by inserting the shunt into the delivery catheter 130. As shown in FIG. 7, the shunt 100 is inserted into the lumen 136 in a substantially linear configuration, and is positioned near the distal end 134 of the delivery catheter 130. In one embodiment, the shunt 100 is preferably collapsible within the lumen 136 so that it has a collapsed dimension for insertion smaller than its expanded dimension when implanted in the patient. The shunt 100 is positioned in the lumen 136 preferably so that the proximal end 106 of the shunt is nearest to the distal end 134 of the delivery catheter, and the distal end 108 of the shunt is nearest to the proximal end 132 of the delivery catheter.

As shown in FIG. 7, a positioning rod 140 assists insertion and positioning of the shunt 100 within the lumen 136 of the delivery catheter. This rod 140 is preferably an elongate body having a proximal end 142 and a distal end 144, and is made of a material with sufficient stiffness to be pushable through the lumen of the delivery catheter 100 without bending back on itself. Moreover, the rod 140 also has sufficient flexibility so that it can bend and navigate through the pathways of the human vasculature. Suitable materials for the rod 140 include biocompatible materials such as nitinol, stainless steel and polymers.

The distal end of the rod 140 is provided with a grasper or clasp 146 for holding the distal end 108 of the shunt 100. More particularly, the clasp 146 is attached to the shunt 100 prior to insertion of the shunt into the delivery catheter. The shunt 100 is preferably delivered by inserting the shunt into the proximal end 132 of the delivery catheter, and pushing distally on the rod 140 outside of the patient until the shunt is at the distal end of the delivery catheter. It will also be appreciated that the shunt 100 may be inserted into the delivery catheter before the delivery catheter is advanced into the patient, either by pushing the shunt through the proximal end of the delivery catheter or by pulling the shunt through the distal end of the delivery catheter.

Figure 8:
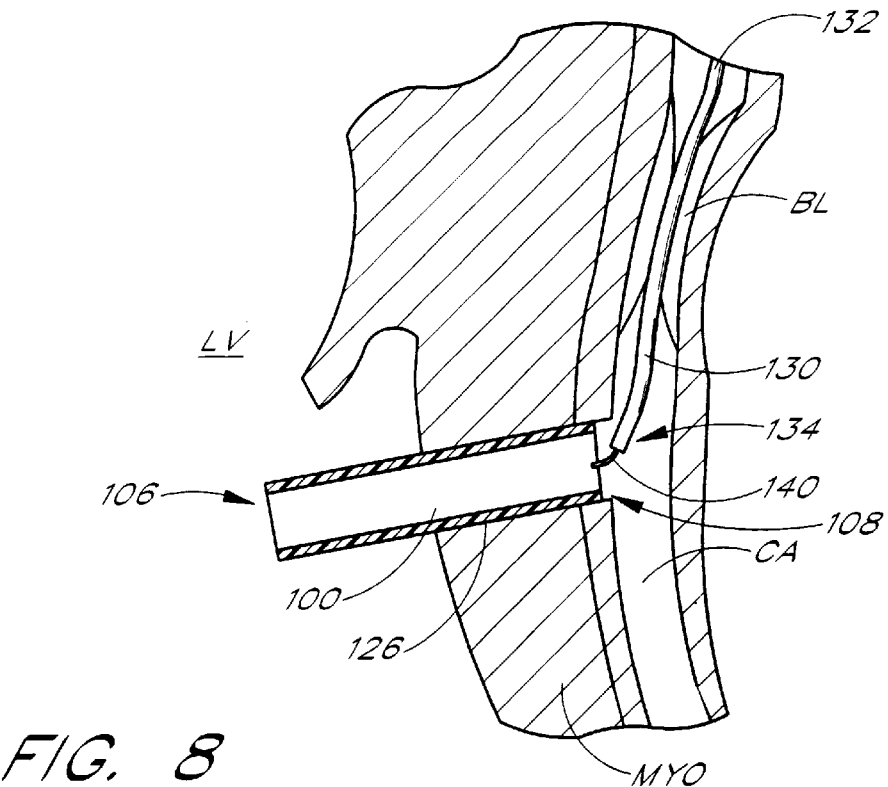
FIG. 8 is a schematic partial cross-sectional view of a coronary artery adjacent the left ventricle, showing a delivery catheter delivering a shunt into the myocardial passageway of FIG. 5.

As shown in FIG. 8, once the shunt 100 is at the distal end 134 of the delivery catheter 130, with the distal end 134 turned at least partially into the passageway 126, the rod 140 is pushed distally to advance the shunt 100 out of the lumen 136 and into the passageway 126. The shunt 100 is preferably constructed from a material having sufficient pushability not only to enable pushing of the shunt through the lumen of the delivery catheter, but also through the passageway 126 formed in the myocardium MYO. It will be appreciated that when the shunt 100 is collapsible within lumen 136, removal of the shunt 100 from the delivery catheter 130, causes the shunt to expand to a size that substantially fills the myocardial passageway 126, as shown in FIG. 8. The rod 140 preferably pushes the shunt 100 completely out of the distal end 134 of the delivery catheter, with the proximal end 106 of the shunt 100 extending past the myocardial wall and into the left ventricle LV. More preferably, the proximal end 106 extends into the left ventricle LV by approximately the distance desired for the section 104 to extend into the coronary artery, as shown in FIG. 1B.

Figure 9:
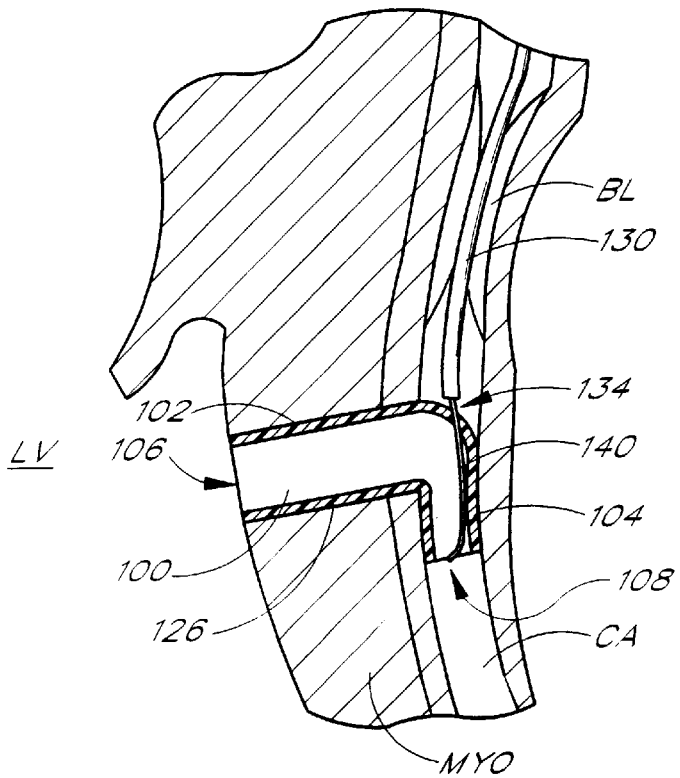
FIG. 9 is a schematic partial cross-sectional view of a coronary artery adjacent the left ventricle, showing the formation of an L-shaped shunt between the left ventricle and coronary artery.

As shown in FIG. 9, the delivery catheter 130 is then preferably pulled back proximally of the passageway 126 so that the lumen 136 at the distal end 134 faces downstream in the coronary artery CA rather than into the passageway 126. The rod 140 is then pulled back proximally to move the distal end 108 of the shunt 100 out of the passageway 126 and into the coronary artery CA. Because the lumen 136 of the delivery catheter faces into the coronary artery CA, pushing distally on the rod 140 as shown in FIG. 9, causes the shunt 100 to bend around the corner between the passageway 126 and the coronary artery CA. The rod 140 is pushed distally until the proximal end 106 of the shunt 100 is substantially flush with the myocardial wall at the left ventricle LV, and the distal end 108 of the shunt 100 lies in the coronary artery CA downstream from the passageway 126. Because in the preferred embodiment the shunt 100 is collapsible, the shunt 100 does not interfere with pushing of the rod 140 downstream into the coronary artery CA.

After the shunt 100 is positioned as described above, the clasp 146 on the rod 140 is actuated at the proximal end of the rod 140 by an operator, outside of the patient, to release the shunt. The rod 140 and delivery catheter 130 are then retracted from the body, leaving the L-shaped shunt in place for a bypass between the left ventricle LV and the coronary artery CA. As implanted, the shunt 100 has a proximal section 102 within the myocardial passageway 126 and a distal section 104 within the coronary artery CA, such as shown in FIG. 1B.

Folded Shunt Technique

Figure 10:
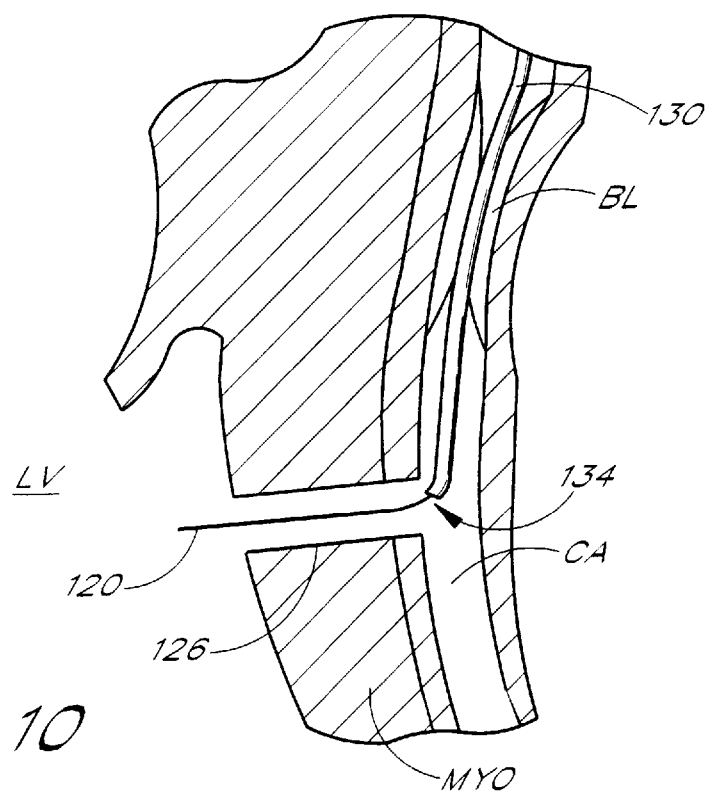
FIG. 10 is a schematic partial cross-sectional view of a coronary artery adjacent the left ventricle, showing a delivery catheter facing partially into the myocardial passageway of FIG. 5 and partially downstream into the coronary artery.

FIG. 10 illustrates another embodiment for delivering an L-shaped shunt into the passageway 126 formed in the myocardium MYO. As with the embodiment shown in FIG. 6, a delivery catheter 130 having a proximal end 132 and a distal end 134 and a lumen 136 (not shown) extending therethrough is advanced over a guidewire 120 toward the passageway 126. Preferably, the delivery catheter 130 is advanced until the distal end 134 extends partially into the passageway 126, such that the lumen 136 at the distal end faces at least partially into the passageway 126. Once the delivery catheter is placed in this position, the guidewire 120 is preferably removed.

Figure 11:
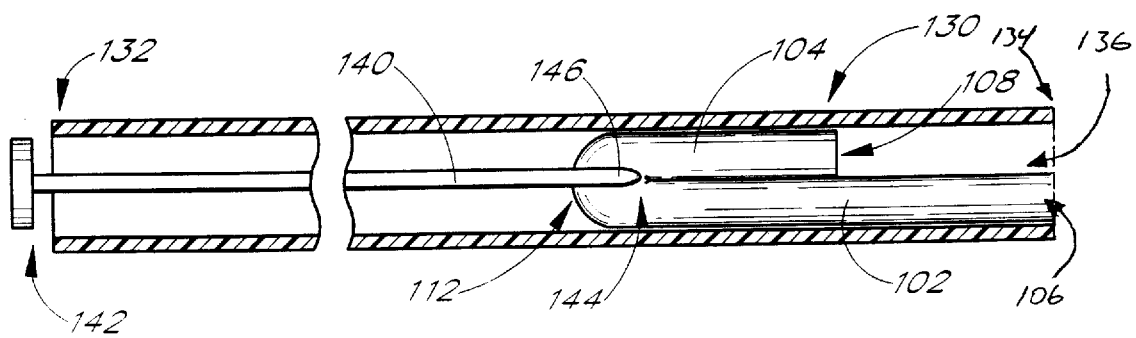
FIG. 11 is a partial cross-sectional view of the delivery catheter of FIG. 10 having a folded shunt inserted therein.

A shunt 100 is positioned at the distal end 134 of the delivery catheter 130 in the lumen 136. As shown in FIG. 11, this shunt is inserted into the catheter and preferably collapsed, such that its proximal end 106 is closest to the distal end 134 of the delivery catheter 130, and its distal end 108 is folded over within the lumen 136. The fold 112 causes the distal end 108 and the proximal end 106 to face in the same distal direction while inserted into the lumen 136 of the delivery catheter. More particularly, the fold 112 in the shunt preferably divides the shunt into a proximal section 102, which is to extend into the passageway 126, and a distal section 104, which is to extend into the coronary artery CA. The location of fold 112 is preferably determined by the length of the passageway 126, and more particularly, is placed such that the proximal section 102 has a length substantially corresponding with the length of the passageway 126.

As described with respect to the pullback technique above, the shunt 100 is preferably collapsible within lumen 136. More preferably, the shunt 100 may be made of a shape memory material such as nitinol to give the shunt 100 a remembered expanded shape such as shown in FIG. 2. In this embodiment, the shunt 100 is collapsed within the lumen 136 from the expanded shape for insertion into the patient.

The folded shunt 100 is preferably loaded into the delivery catheter through use of rod 140, as illustrated in FIG. 11. This rod 140 is similar to the rod described with respect to FIG. 7 above, more particularly having a proximal end 142 and a distal end 144. A clasp 146 is provided at the distal end of the rod 140, which grasps the shunt 100 at about the fold 112. The shunt 100 is preferably loaded into the delivery catheter 130 through the proximal end 132 after the delivery catheter has reached its position shown in FIG. 11 by pushing distally on the rod 140 which is attached to the shunt 100. It will be appreciated, however, that the shunt may be loaded prior to inserting the delivery catheter 130 into the patient, either by pushing through the proximal end 132 or pulling through the distal end 134.

Figure 12:
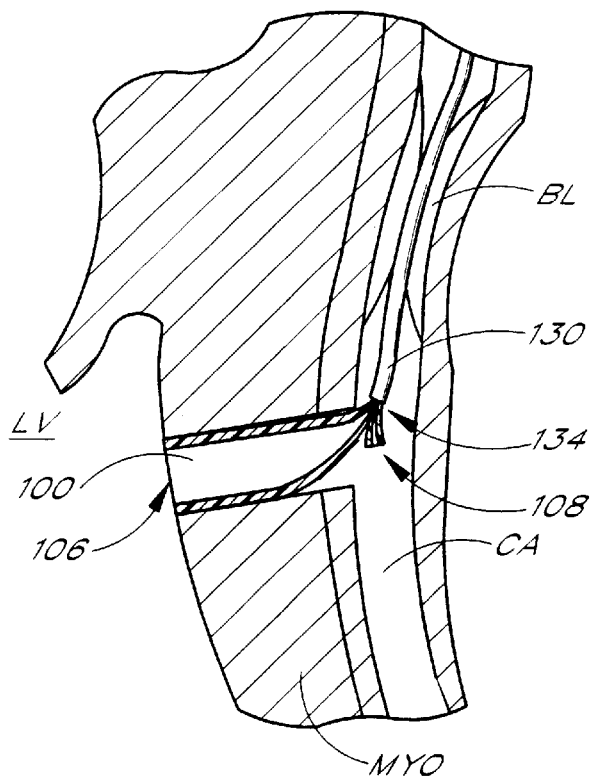
FIG. 12 is a schematic partial cross-sectional view of a coronary artery adjacent the left ventricle, showing a delivery catheter delivering the proximal section of an L-shaped shunt into the myocardial passageway of FIG. 5.

Once the shunt 100 has reached the distal end 134 of the delivery catheter 130, the delivery catheter is turned, if necessary, to ensure that the proximal section 102 of the shunt 100 is in the part of the lumen 136 closest to the passageway 126. With the distal end of the delivery catheter facing at least partially into the passageway 126, when the rod 140 is pushed distally to advance the shunt 100 out of the delivery catheter 130, this positioning causes the proximal section 102 of the shunt to exit the delivery catheter first into the passageway 126, as shown in FIG. 12. As the proximal section 102 exits the lumen 136, the shunt 100 begins to expand toward its expanded shape.

Figure 13:
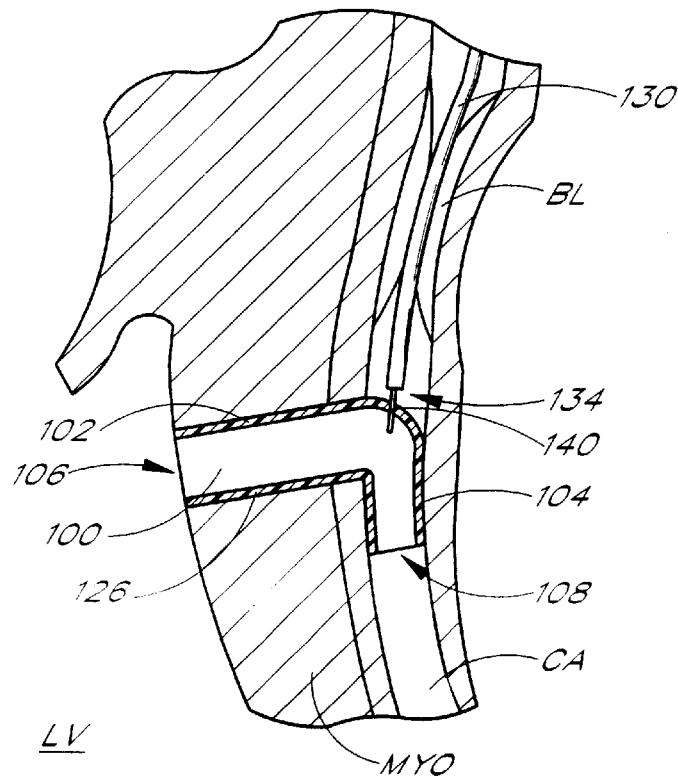
FIG. 13 is a schematic partial cross-sectional view of a coronary artery adjacent the left ventricle, showing a delivery catheter delivering the distal section of an Lshaped shunt into the coronary artery.

As the rod 140 pushes the shunt 100 further distally out of the delivery catheter 130, the distal section 104 of the shunt exits into the coronary artery CA because of the placement of the distal section 104 within the lumen 136 away from the myocardium. In one embodiment, when the delivery catheter 130 is delivered, the lumen 136 of the distal end 134 faces partially into the passageway 126, and partially into the coronary artery CA, as shown in FIG. 10. Then, because the catheter 130 is turned, as necessary, to position the proximal section 102 of the shunt 100 in the part of the lumen 136 facing the passageway 126, correspondingly, the distal section 104 is positioned in the part of the lumen 136 that faces into the coronary artery CA. This allows the distal section 104 to exit the delivery catheter 130 into the coronary artery CA. To further assist in delivering the distal section 104 into the coronary artery CA, the delivery catheter 130 may be pulled proximally back once the proximal section 102 enters the passageway 126 so that the lumen 136 at the distal end 134 faces only downstream into the coronary artery CA. As shown in FIG. 13, when the distal end of the rod 140 is pushed out of the delivery catheter 130, the proximal section 102 has extended completely through the passageway 126 such that proximal end 106 of the shunt 100 is approximately flush with the myocardial wall at the left ventricle LV. The distal section 104 extends into the coronary artery CA downstream from the passageway 126. Once in this position, the clasp 146 is removed from the shunt 100 and the delivery catheter 130 and rod 140 are removed.

It will be appreciated that the position of the delivery catheter 130 may be moved during delivery of the shunt 100 to ensure that the proximal section 102 is delivered into the passageway 126 and the distal section is delivered into the coronary artery CA. For example, the delivery catheter 130 may be pushed further into the passageway 126 prior to delivering the proximal section of the shunt 100 therein. Then, prior to delivery of the distal section 104, the delivery catheter 130 may be pulled proximally back so that the lumen 136 at the distal end 134 faces downstream into the coronary artery CA.

The embodiments illustrated and described above are provided merely as examples of certain preferred embodiments of the present invention. Other changes and modifications can be made from the embodiments presented herein by those skilled in the art without departure from the spirit and scope of the invention, as defined by the appended claims.

What is claimed is:

1. A method for delivering a conduit between a chamber of a heart and a blood vessel adjacent the chamber, the method comprising:

providing a conduit having a first end and a second end;

advancing the conduit through a patient's vascular system to the heart;

placing the first end of the conduit through a passageway formed in a myocardial wall surrounding the heart chamber; and placing the second end of the conduit in the blood vessel, wherein the blood vessel joins the passageway generally at an angle, and the conduit bends between the first end and the second end.

2. The method of claim 1, wherein placing the second end in the blood vessel includes placing the second end in a portion of the blood vessel downstream from the passageway.

3. The method of claim 1, wherein the blood vessel is a coronary artery and the heart chamber is a left ventricle.

4. The method of claim 1, further comprising providing a delivery catheter, wherein advancing the conduit through the vascular system includes advancing the conduit via the delivery catheter.

5. The method of claim 1, further comprising forming the passageway in the myocardial wall.

6. The method of claim 1, wherein the conduit is made of semi-rigid material.

7. The method of claim 1, wherein the conduit has a unitary construction.

8. The method of claim 1, wherein the conduit is made of a plurality of sections joined together prior to the advancing of the conduit.

9. The method of claim 1, wherein advancing the conduit includes advancing the conduit in a folded configuration to the heart.

10. The method of claim 1, wherein advancing the conduit includes advancing the conduit in a substantially straight configuration to the heart.

11. The method of claim 1, wherein advancing the conduit includes advancing the conduit in a collapsed configuration to the heart and wherein placing the first end and the second end includes expanding the conduit.

12. The method of claim 1, wherein the conduit is made of a shape memory material.

13. The method of claim 1, wherein advancing the conduit includes advancing the conduit through the blood vessel to the heart.

14. The method of claim 13, the blood vessel is a coronary artery.

15. The method of claim 1, wherein the conduit defines a first opening in the first end and a second opening in the second end, and wherein placing the first end includes placing the first opening in flow communication with the heart chamber.

16. The method of claim 15, wherein the heart chamber is a left ventricle and the blood vessel is a coronary artery.

* * * * *

UNITED STATES PATENT AND TRADEMARK OFFICE
CERTIFICATE OF CORRECTION

PATENT NO. : 6,582,444 B2
DATED : June 24, 2003
INVENTOR(S) : Peter J. Wilk

It is certified that error appears in the above-identified patent and that said Letters Patent is hereby corrected as shown below:

Column 10,
Line 28, replace "claim 13" with -- claim 13, wherein the --.

Signed and Sealed this

Sixteenth Day of September, 2003

JAMES E. ROGAN
*Director of the United States Patent and Trademark Office*